United States Patent [19]

Cremascoli

[11] Patent Number: 4,957,510
[45] Date of Patent: Sep. 18, 1990

[54] HIP PROSTHESIS STRUCTURE ADAPTED FOR EASY FITTING TO THE PATIENT COXO-FEMURAL ARTICULATION

[76] Inventor: Patrizio Cremascoli, Via Clemente Prudenzio, 14/16 -- 20138 Milan, Italy

[21] Appl. No.: 224,454

[22] Filed: Jul. 26, 1988

[30] Foreign Application Priority Data

Aug. 3, 1987 [IT] Italy ................................ 12023 A/87

[51] Int. Cl.$^5$ .............................................. A61F 2/36
[52] U.S. Cl. ......................................... 623/23; 623/22
[58] Field of Search ........................................... 623/23

[56] References Cited

U.S. PATENT DOCUMENTS

Re. 32,488   9/1987   Gustilo et al. ......................... 623/23
3,938,198    2/1976   Kahn et al. ............................ 623/23
4,664,668    5/1987   Beck et al. ............................ 623/23

FOREIGN PATENT DOCUMENTS 0201407  11/1986   European Pat. Off. ............. 623/23
0243298  10/1987   European Pat. Off. ............. 623/23

*Primary Examiner*—Randall L. Green
*Assistant Examiner*—Stephanie L. Iantorno
*Attorney, Agent, or Firm*—Bucknam and Archer

[57] ABSTRACT

This prosthesis essentially comprises a given size stem at the top portion thereto there is provided an oval cross-section seat for firmly coupling one oval end of a coupling bar, the other frustum of cone shaped end of which bears a spherical head to be coupled to a hip acetabulum, the coupling bar having a variable length and a longitudinal axis of any given angle of inclination.

1 Claim, 3 Drawing Sheets

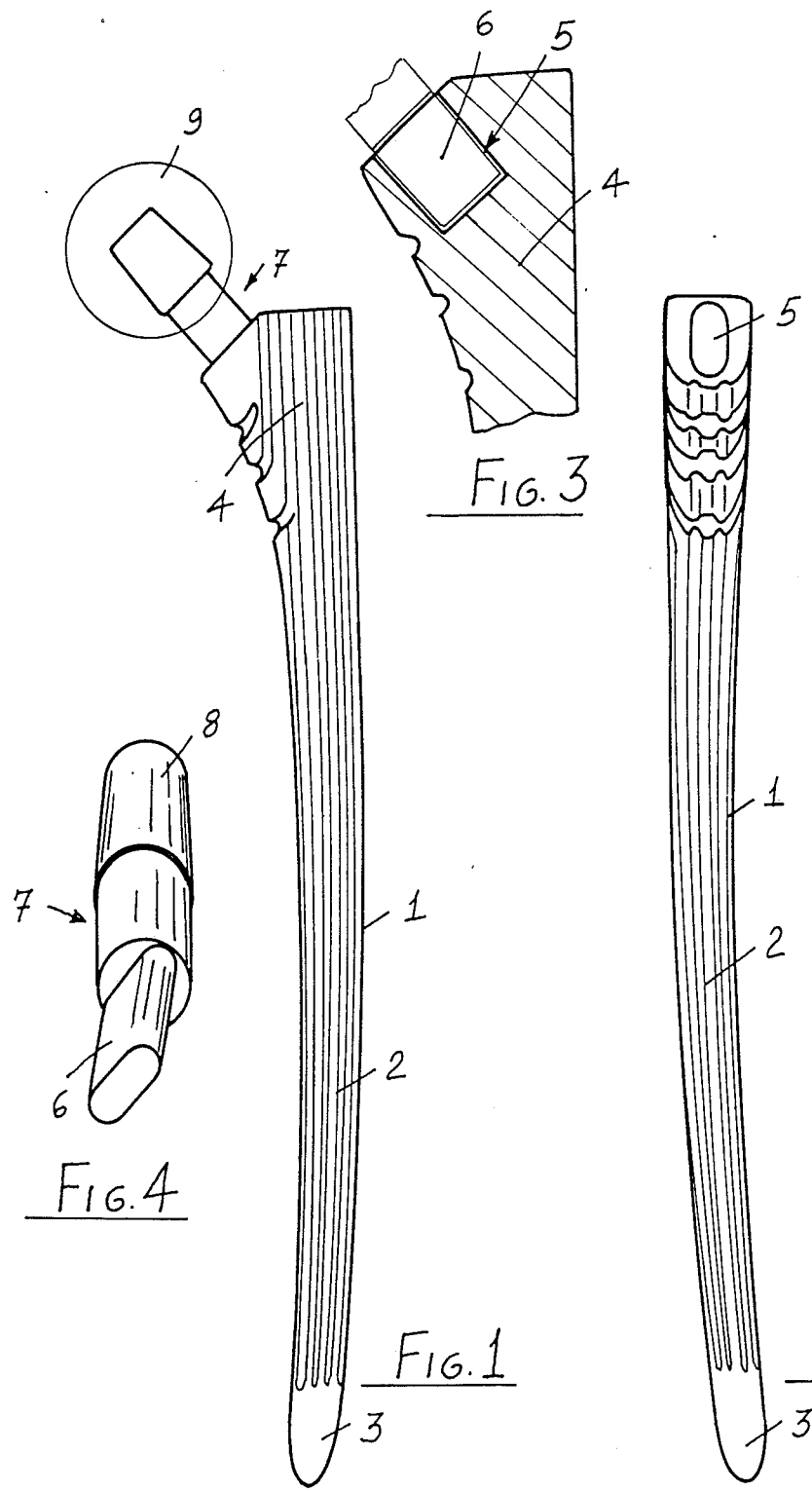

HIP PROSTHESIS STRUCTURE ADAPTED FOR EASY FITTING TO THE PATIENT COXO-FEMURAL ARTICULATION

BACKGROUND OF THE INVENTION

The present invention relates of a hip prosthesis structure, which is adapted to be easily fitted to the specific shape or geometrical characteristics of the patient coxo-femural articulation.

As is known in the case of fractures, arthritis and the like of the human hip or its articulated joint with the femur, there are conventionally used suitable hip prosthesis in order to provide the hip joint with renewed mobility.

Conventional hip prosthesis structures are usually made as a single piece, consisting of a stem from the top portion of which a coupling portion extends thereon there is applied a spherical head, provided for engaging in the femur acetabulum.

The thus constructed prosthesis, however, have the drawback that they can not be used for all of the patients, unless said prostheses are specifically adapted in size to the geometrical structure of the hip and femur of the patient.

In fact, these prostheses, though they have been tailored in a satisfactory way for a given patient, can not be adapted to other patients mainly because their coupling portions have a greater or smaller length than that suitable for providing a proper coxofemural articulation.

In these cases, as it should be apparent, the prosthesis head can not be properly fitted to the patient acetabulum therewith it should cooperate.

Sometimes, moreover, the patient has a so-called "varus" femur, that is having a rather anomalous shape, and for these femurs particular hip prostheses must be adopted in which the coupling portion has a specific preset orientation with respect to the stem.

In this connection, it should be moreover pointed out that the femur coupling portion is not perpendicular to the patient pelvis thereby a normal coupling portion is reversed at about 10° with respect to the pelvis.

Known hip prostheses, on the other hand, are not designed to overcome this drawback and hence they cannot be adapted in a perfect way to the anatomic characteristics of a lot of patients.

SUMMARY OF THE INVENTION

Accordingly, the task of the present invention is to overcome the above mentioned drawbacks by providing a hip prosthesis which can be provided with a coupling portion or member of any desired length, according to requirements.

Within the scope of the above mentioned object, a main object of the present invention is to provide such a hip prosthesis in which the axis of the coupling portion can form a different opening angle with respect to the axis of the stem.

Yet another object of the present invention is to provide such a hip prosthesis structure in which the axis of the coupling portion has any desired angle of inclination.

According to one aspect of the present invention, the above mentioned task and objects, as well as yet other objects, which will become more apparent hereinafter, are achieved by a hip prosthesis structure characterized in that it essentially comprises a give size stem at the top portion of which there are provided means for firmly coupling one end of a shaped bar or coupling member bearing a spherical head to be coupled to the patient pelvis acetabulum, said shaped bar having a variable length and a longitudinal axis having any desired angle of inclination.

BRIEF DESCRIPTION OF THE DRAWINGS

Further characteristics and advantages of the hip prosthesis structure according to the present invention will become more apparent from the following detailed description of a preferred though not exclusive embodiment thereof, which is illustrated, by way of an indicative example, in the figures of the accompanying drawings, in which:

FIG. 1 is a side view of the hip prosthesis structure according to the present invention;

FIG. 2 shows a front view of the prosthesis stem;

FIG. 3 is a cross-sectional view illustrating the coupling between the stem and coupling member of the prosthesis;

FIG. 4 shows a possible embodiment of the prosthesis coupling member;

DESCRIPTION OF THE PREFERRED EMBODIMENTS

Figure 5:
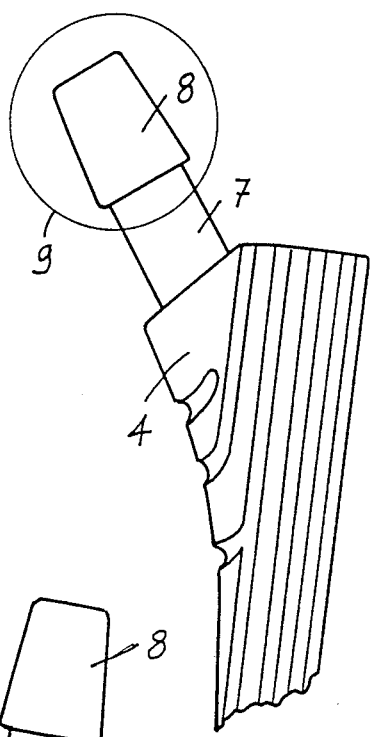
FIGS. 5 to 9 show other possible embodiments of necks adapted to be applied on the prosthesis stem and having different extension longitudinal axes.
Figure 6:
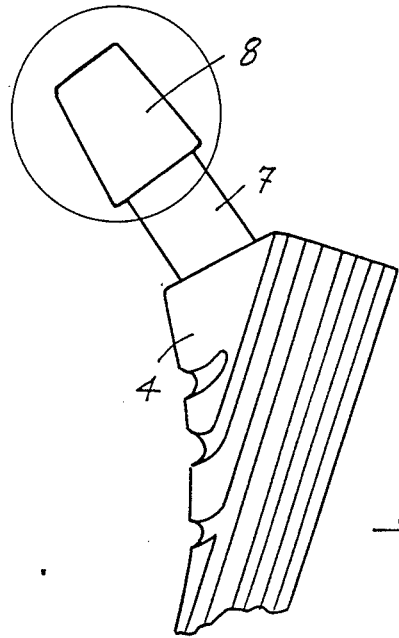
Figure 7:
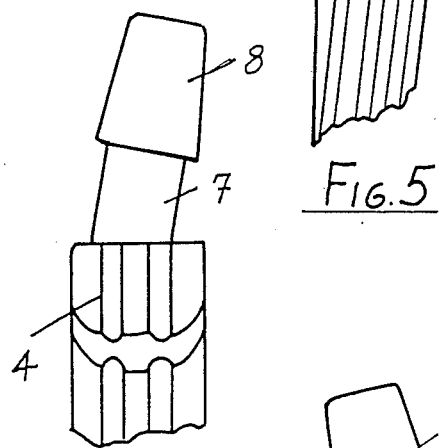
Figure 8:
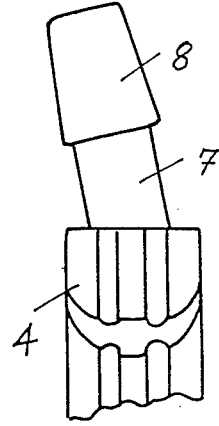

With reference to the above figures of the accompanying drawings, the hip prosthesis structure according to the present invention essentially comprises a stem 1, consisting of a flat bar, having a given length and a surface provided with a plurality of longitudinal slots 2.

The prosthesis stem, in particular, extends according to a suitably curved longitudinal axis and has its bottom end 3 of substantially oval shape.

The stem is moreover provided, at the top thereof, of a portion 4 enlarged at the side of its concave perimetrical line on which there is formed a seat or recess 5 having a suitably slanted axis an oval cross-section and suitably tapered.

As is clearly shown in FIGS. 1 to 3, the enlarged portion 4 has a grooved slanted face in which there are formed a plurality (three in the shown embodiment) of spaced grooves which have been specifically designed for receiving the femur bone ingrowth so as to provide, in cooperation with the mentioned slots 2, a very firm gripping of the stem 1 in the femur (not shown).

In the seat there can be firmly housed one end 6, also of oval cross-section, of a small bar or coupling member 7 the other end 8 of which has a frustum of cone shape to firmly restrain a spherical head 9 adapted in turn for coupling with the acetabulum of the pelvis of the patient.

In this connection it should be pointed out that the mentioned small bar may have any desired variable length, depending on the specific use requirements.

The mentioned small bar, moreover, may have a differently slanted axis, with respect to its end engaging in the seat 5 of the stem and the axis of which, of course, will coincide with the axis of said seat.

This slanting can be essentially obtained according to any of the planes pertaining to the plane set passing through the line defining the axis of said seat.

Figure 9:
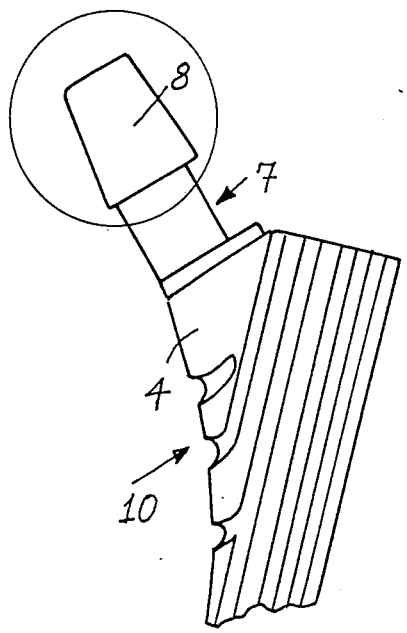

More specifically, as is shown in FIG. 9, an embodiment of the present invention provides for the use of a coupling member including an insertion end which is offset from its axial extension.

Thus, a prosthesis will be formed including a coupling member which virtually constitutes an extension of the middle curvature, indicated at 10, of the top portion of the stem.

This configuration will afford the possibility of inserting a coupling member even in prostheses of minimum thickness, while assuring a perfect and reproducible positioning of the stem-coupling member assembly, without any risks of a possible disengaging of the two parts.

Figure 10:
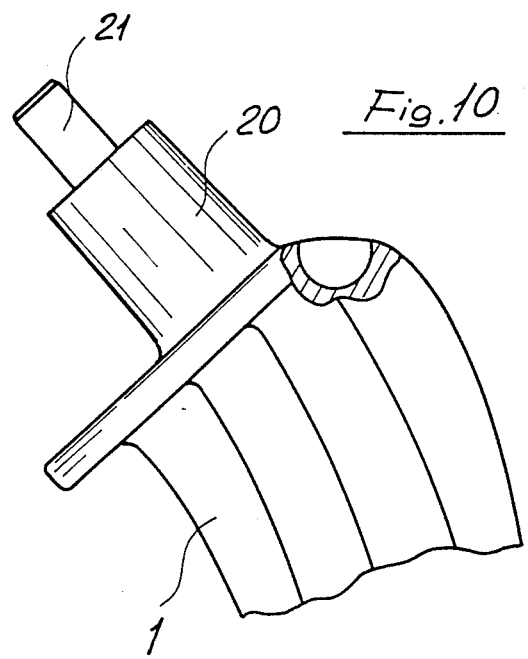
FIG. 10 shows another embodiment of the prosthesis stem, at the coupling end with the prosthesis coupling member.
Figure 11:
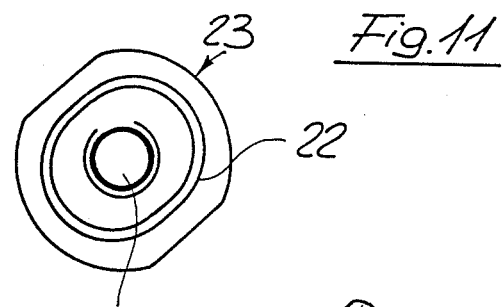
FIGS. 11 and 12 are respectively an end view and a cross-sectional view of the coupling member to be used with the prosthesis stem illustrated in FIG. 10.
Figure 12:
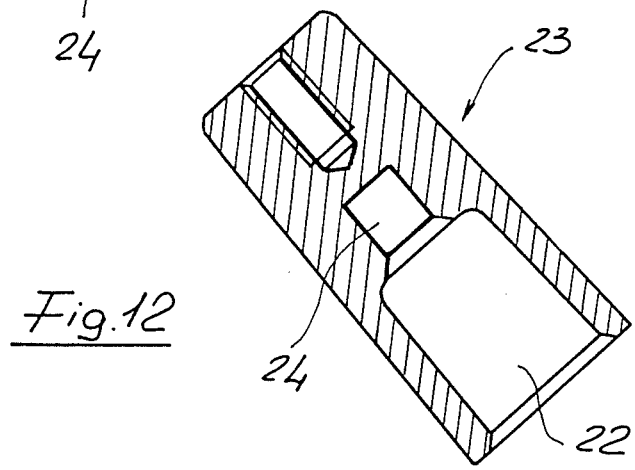

FIGS. 10 to 12 show another possible embodiment in which, at the enlarged end of the stem 1 there is provided a lug 20, which has a substantially tapering shape and an elliptical cross-section.

From the lug 20 a cylindrical portion 21 may project, said cylindrical portion being arranged on the axial extension of said lug 20.

More specifically, said lug 20 can be engaged and firmly locked in a counter-shaped hollow 22, formed at the axial end portion of a coupling member of the prosthesis, indicated at 23.

If desired the hollow 22 may be provided with a recess 24 for housing the mentioned cylindrical portion 21.

From the above disclosure it should be apparent that the invention fully achieves the intended objects.

While the invention has been disclosed and illustrated with reference to a preferred embodiment thereof, it should be apparent that the disclosed embodiment is susceptible to several modifications and variations all of which will come within its scope and spirit.

I claim:

1. A hip prosthesis comprising an elongated oval cross-section stem, said stem having a first set curvature, a plurality of longitudinal extending slots formed on said stem, said stem including a first pointed end portion and an opposite enlarged second end portion, said enlarged portion having a second set curvature different from said first set curvature of said stem, a plurality of spaced bone gripping grooves formed on said enlarged end portion, an oval cross-section seat formed in said enlarged portion and a coupling element for coupling said stem to a prosthesis head, said coupling element including a middle body and two coupling element end portions integral with and on opposite ends of said middle body, one of said end portions having an oval cross-section for engaging in said seat and the other of said end portions having a frustum of cone shape, said coupling element being so designed that, as said oval cross-section end of said coupling element is engaged in said seat, said middle body and said other end portion of said coupling element provide an extension having a curvature substantially corresponding to said second set curvature of said enlarged end portion of said stem.

* * * * *